US00PP29381P2

(12) United States Plant Patent
Bentley

(10) Patent No.: US PP29,381 P2
(45) Date of Patent: Jun. 12, 2018

(54) ARMERIA PLANT NAMED 'DAYDREAM'

(50) Latin Name: *Armeria pseudarmeria*
Varietal Denomination: Daydream

(71) Applicant: Plant Growers Australia Pty Ltd, Wonga Park (AU)

(72) Inventor: Howard Bentley, Lilydale (AU)

(73) Assignee: Plant Growers Australia Pty Ltd, Wonga Park (AU)

( * ) Notice: Subject to any disclaimer, the term of this patent is extended or adjusted under 35 U.S.C. 154(b) by 0 days. days.

(21) Appl. No.: 15/731,340

(22) Filed: May 30, 2017

(51) Int. Cl.
*A01H 5/00* (2018.01)

(52) U.S. Cl.
USPC ..... Plt./263.1
CPC ..... *A01H 5/00* (2013.01)

(58) Field of Classification Search
USPC ..... Plt./263.1
CPC ..... A01H 5/00
See application file for complete search history.

*Primary Examiner* — Kent L Bell
(74) *Attorney, Agent, or Firm* — Audrey Charles

(57) ABSTRACT

A new and distinct cultivar of *Armeria* plant named 'Daydream', characterized by its medium purplish-pink colored flowers, dark green-colored foliage, and moderately vigorous, compact-mounded growth habit, is disclosed.

1 Drawing Sheet

Latin name of genus and species of plant claimed: *Armeria pseudarmeria.*

Variety denomination: 'Daydream'.

BACKGROUND OF THE INVENTION

The present invention relates to a new and distinct cultivar of *Armeria* plant botanically known as *Armeria pseudarmeria* and hereinafter referred to by the cultivar name 'Daydream'.

The new cultivar originated in a controlled breeding program in Wonga Park, Australia during October 2009. The objective of the breeding program was the development of *Armeria* cultivars that have an extended flowering season, shorter peduncles and a compact-mounded habit.

The new interspecific *Armeria* cultivar is the result of cross-pollination. The female (seed) parent of the new cultivar is a proprietary *Armeria pseudarmeria* breeding selection, coded IB910-7, not patented, characterized by its dark pink-colored flowers, medium green-colored foliage, and moderately vigorous, mounded growth habit. The male (pollen) parent of the new cultivar is a proprietary *Armeria pseudarmeria* breeding selection, coded IB910-14, not patented, characterized by its light pink-colored flowers, medium green-colored foliage, and moderately vigorous, mounded growth habit. The new cultivar was discovered and selected as a single flowering plant within the progeny of the above stated cross-pollination during February 2011 in a controlled environment in Wonga Park, Australia.

Asexual reproduction of the new cultivar by division since February 2011 in Wonga Park, Australia and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Daydream' as a new and distinct cultivar of *Armeria* plant:

1. Medium purplish-pink colored flowers;
2. Dark green-colored foliage; and
3. Moderately vigorous, compact-mounded growth habit.

Plants of the new cultivar differ from plants of the female parent primarily in having a lighter flower color, shorter peduncles and a more compact habit. Plants of the new cultivar differ from plants of the male parent primarily in having shorter peduncles, greater quantity of leaves per clump, and a longer flowering season.

Of the many commercially available *Armeria* cultivars, the most similar in comparison to the new cultivar is 'Bees Ruby', not patented. However, in comparison, plants of the new cultivar differ from plants of 'Bees Ruby' in at least the following characteristics:

1. Plants of the new cultivar have a lighter flower color than plants of 'Bees Ruby';
2. Plants of the new cultivar have shorter peduncles than plants of 'Bees Ruby'; and
3. Plants of the new cultivar have a longer flowering season than plants of 'Bees Ruby'.

In addition the new cultivar can be compared to Dreameria 'Sweet Dreams', co-pending U.S. Plant patent application Ser. No. 15/731,341. However, in side-by-side comparison, plants of the new cultivar differ from plants of 'Sweet Dreams' in at least the following characteristics:

1. Plants of the new cultivar have a flower color different from plants of 'Sweet Dreams';
2. Plants of the new cultivar are taller than plants of 'Sweet Dreams'; and
3. Plants of the new cultivar have fewer flowers per inflorescence than plants of 'Sweet Dreams'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Daydream'. The plants were grown in one-gallon containers for approximately seven months in a glass-covered greenhouse in Elburn, Ill.

DETAILED BOTANICAL DESCRIPTION

Figure 1:
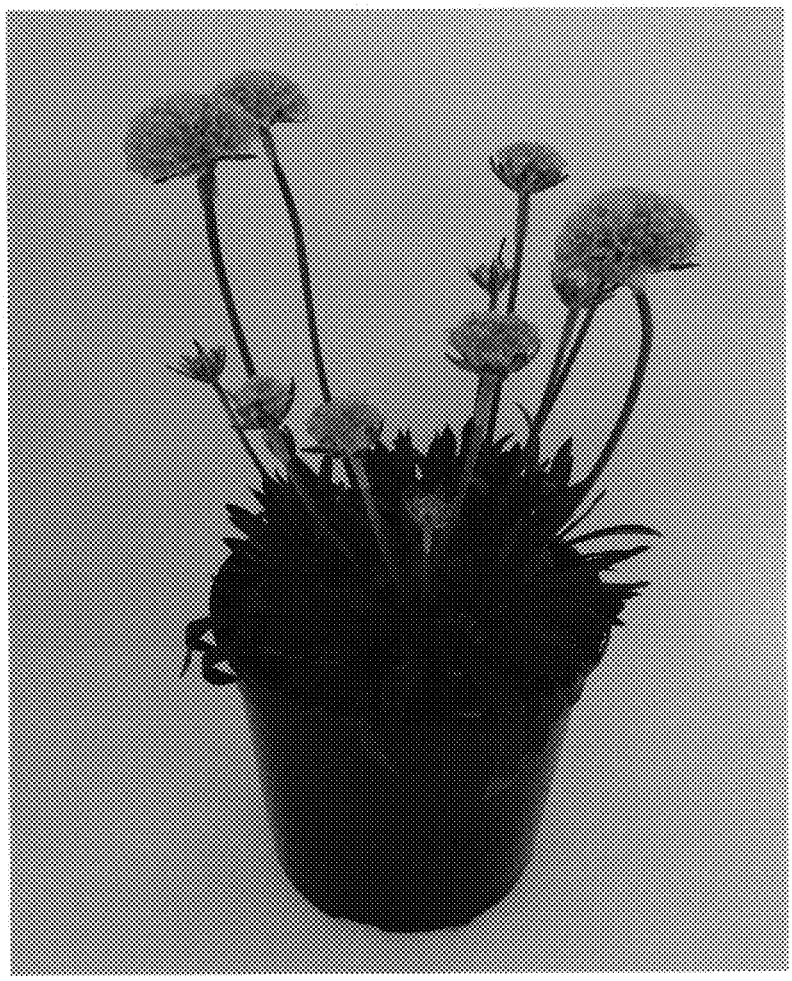
FIG. 1 illustrates a side view of the overall growth and flowering habit of 'Daydream'.
Figure 2:
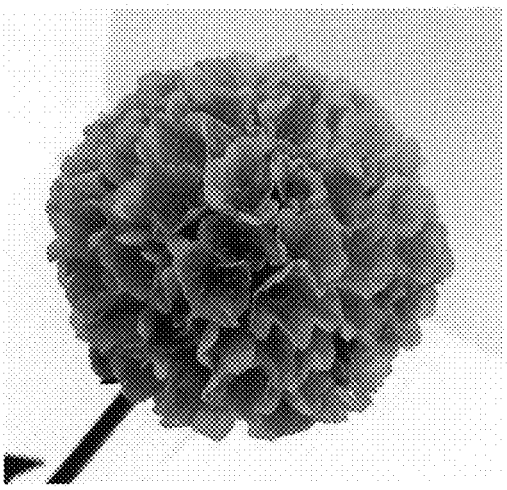
FIG. 2 illustrates a close-up view of an individual inflorescence of 'Daydream'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2017 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in one-gallon containers for approximately seven months in Elburn, Ill. Plants were transplanted in late fall from rooted cuttings. Greenhouse temperatures were maintained during the winter months at approximately 45° F. to 65° F. (7.2° C. to 18.3° C.) during the day and approximately 35° F. to 45° F. (1.7° C. to 7.2° C.) during the night. For the final 12 weeks, greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Armeria pseudarmeria* cultivar Daydream.

Parentage:

*Female and male parent*.—Proprietary *Armeria pseudarmeria* breeding selection coded IB910-7, not patented.

*Female and male parent*.—Proprietary *Armeria pseudarmeria* breeding selection coded IB910-14, not patented.

Propagation:

*Type cutting*.—Terminal.

*Time to initiate roots*.—Approximately 15 to 18 days.

*Time to produce a rooted cutting*.—Approximately 6 to 7 weeks.

*Root description*.—Fine, fibrous.

*Rooting habit*.—Freely branching.

Plant description:

*Commercial crop time*.—Approximately 14 to 16 weeks from a rooted cutting to finish in a 15 cm pot, vernalization not required for flowering.

*Growth habit and general appearance*.—Herbaceous perennial, moderately vigorous, compact-mounded.

*Hardiness*.—USDA Zone 6a (−10° F. to −5° F./−23.3° C. to −20.6° C.).

*Size*.—Height from soil level to top of plant plane: Approximately 27.5 cm. Height from soil level to top of foliage: Approximately 9.0 cm. Width: Approximately 20.5 cm.

*Branching habit*.—Clump forming. Quantity of main clumps per plant: Approximately 10.

Foliage description:

*General description*.—Quantity of leaves per main clump: Approximately 12. Fragrance: None. Form: Simple. Arrangement: Basal rosette.

*Leaves*.—Shape: Oblanceolate. Margin: Entire. Apex: Acute. Base: Attenuate, sessile. Venation pattern: Parallel. Length of mature leaf: Approximately 9.0 cm. Width of mature leaf: Approximately 1.3 cm. Texture of upper and lower surfaces: Glabrous. Color of upper surface of young foliage: NN137A, base of NN155D, glaucous, venation indistinguishable from laminae. Color of lower surface of young and mature foliage: 137B with 137A, base of NN155D, glaucous, venation indistinguishable from laminae. Color of upper surface of mature foliage: NN137A with 139A, base of NN155D, glaucous, venation indistinguishable from laminae.

Flowering description:

*Flowering habit*.—'Daydream' is freely flowering under outdoor growing conditions with substantially continuous blooming from spring through autumn.

*Lastingness of inflorescence on the plant*.—Color holds for approximately 2 weeks.

Inflorescence description:

*General description*.—Type: Head, globose, terminal on scape, facing upright. Quantity per plant: Approximately 8. Fragrance: None detected. Length or height: Approximately 2.5 cm. Width: Approximately 4.0 cm. Quantity of fully open flowers per inflorescence: Approximately 75.

*Scape*.—Strength: Strong. Aspect: Erect. Length: Approximately 22.5 cm. Diameter: Approximately 4.0 mm. Texture: Glabrous. Color: 137B maturing to NN137A, glaucous. Involucral sheath length: Approximately 2.0 cm.

*Involucral bracts*.—Quantity: 18, in multiple whorls. Aspect: Cupped to flat. Shape: Lanceolate to oblong. Margin: Entire. Apex: Acute. Base: Truncate. Length of outermost: Approximately 2.0 cm. Width of outermost: Approximately 5.0 mm. Length of innermost: Approximately 1.3 cm. Width of innermost: Approximately 5.0 mm. Texture of upper and lower surfaces: Glabrous. Color of upper (inner) surface: 137B with 144A at base and transparent, colorless margins. Color of lower (outer) surface: 137A with 144A at base and transparent, colorless margins, outermost glaucous.

Flower description:

*Type*.—Salverform, in clusters of four.

*Bud*.—Rate of opening: Generally takes 5 to 6 days for bud to progress from first color to fully open flower.

*Bud just before opening*.—Shape: Tubular. Length: Approximately 7.0 mm. Width: Approximately 3.0 mm. Color: Sepal centers of 145C with transparent, colorless margins; petals of 67D.

*Corolla*.—Length: Approximately 1.1 cm. Width: Approximately 1.3 cm.

*Petals*.—Quantity: 5. Shape: Obovate. Margin: Entire. Apex: Obtuse. Base: Attenuate. Length: Approximately 1.1 cm. Width: Approximately 4.0 mm. Color of upper surface when first open: 67C with base of NN155D. Color of lower surface when first open: 67D with base of NN155D. Color of upper surface when fully open: 65A with base of NN155D. Color of lower surface when fully open: 65B with base of NN155D.

*Calyx*.—Shape: Cupped. Diameter: Approximately 6.0 mm.

*Sepals*.—Quantity per flower: 5, fused sides and base to form a tube. Shape: Obovate. Margin (unfused portion): Entire, wavy. Apex: Aristate. Length: Approximately 8.0 mm. Width: Approximately 2.5 mm. Texture of inner surface: Glabrous. Texture of outer surface: Sparsely pubescent. Color of inner and outer surfaces: Centers of 145A and 145C with transparent, colorless margins.

*Pedicel*.—Strength: Strong, flexible. Length: Approximately 5.0 mm. Diameter: Less than 1.0 mm. Texture: Glabrous. Color: 145D.

*Reproductive organs*.—Androecium: Stamen quantity: 5 per flower. Stamen length: Approximately 8.0 mm. Filament color: NN155D. Anther shape: Oblong, dorsifixed. Anther length: Approximately 1.0 mm. Anther color: 154C. Pollen amount: Moderate. Pollen color: 2C. Gynoecium: Pistil quantity: 1 per flower, with 5 distinct styles. Pistil length: Approximately 9.0 mm. Stigma shape: Pointed. Stigma color: 67D. Style length: Approximately 8.0 mm. Style color: NN155D with a faint overlay of 67D near stigma. Style texture: Glabrous with feather-like pubescence located in lower third. Ovary diameter: Approximately 1.0 mm. Ovary color: 144C.

Seed and fruit production: Neither seed nor fruit production has been observed.

Disease and pest resistance: Resistance to pathogens and pests common to *Armeria* has not been observed.

What is claimed is:

1. A new and distinct cultivar of *Armeria* plant named 'Daydream', substantially as herein illustrated and described.

* * * * *